US010603156B2

(12) United States Patent
Allen et al.

(10) Patent No.: US 10,603,156 B2
(45) Date of Patent: Mar. 31, 2020

(54) BIODEGRADABLE VASCULAR GRAFTS

(71) Applicant: University of Pittsburgh—Of the Commonwealth System of Higher Education, Pittsburgh, PA (US)

(72) Inventors: Robert Andrew Allen, Pittsburgh, PA (US); Chelsea Elizabeth Stowell, Pittsburgh, PA (US); Yadong Wang, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/736,728

(22) PCT Filed: Jun. 16, 2016

(86) PCT No.: PCT/US2016/037790
§ 371 (c)(1),
(2) Date: Dec. 14, 2017

(87) PCT Pub. No.: WO2016/205462
PCT Pub. Date: Dec. 22, 2016

(65) Prior Publication Data
US 2018/0185131 A1    Jul. 5, 2018

Related U.S. Application Data

(60) Provisional application No. 62/182,331, filed on Jun. 19, 2015.

(51) Int. Cl.
*A61F 2/07* (2013.01)
*A61L 27/18* (2006.01)
(Continued)

(52) U.S. Cl.
CPC .................. *A61F 2/07* (2013.01); *A61F 2/06* (2013.01); *A61L 27/14* (2013.01); *A61L 27/18* (2013.01);
(Continued)

(58) Field of Classification Search
CPC ...... A61F 2/06; A61F 2/07; A61F 2210/0076; A61F 2210/0004; A61F 2250/0067;
(Continued)

(56) References Cited

U.S. PATENT DOCUMENTS 5,637,113 A  *  6/1997  Tartaglia .................. A61F 2/07
                                                                604/104
8,048,446 B2    11/2011  Lelkes et al.
(Continued)

FOREIGN PATENT DOCUMENTS

WO    WO 2012/015623    2/2012
WO    WO 2012/078472    6/2012
(Continued)

OTHER PUBLICATIONS

Wang, "Bioelastotriers in Tissue Engineering: Applications in Cardiovascular Tissue," from *Biomaterials for Tissue Engineering Applications: A Review of the Past and Future Trends*, ed. Burdick and Mauck, p. 100, Jan. 2011.
(Continued)

*Primary Examiner* — Paul B Prebilic
(74) *Attorney, Agent, or Firm* — Klarquist Sparkman, LLP (57) ABSTRACT

A vascular graft that includes a biodegradable polyester electrospun tubular core; a biodegradable polyester outer sheath surrounding the biodegradable polyester tubular core; and a biodegradable poly(lactide) copolymer adhesive composition (i) disposed between the polyester electrospun tubular core and the polyester outer sheath, (ii) disposed
(Continued)

between the polyester electrospun tubular core and the polyester outer sheath and on an outer surface of the of the polyester outer sheath, (iii) or disposed on an outer surface of the polyester outer sheath.

30 Claims, 2 Drawing Sheets

(51) Int. Cl.

| | |
|---|---|
| A61L 27/54 | (2006.01) |
| A61F 2/06 | (2013.01) |
| D01D 5/00 | (2006.01) |
| D01F 11/04 | (2006.01) |
| A61L 27/58 | (2006.01) |
| A61L 27/50 | (2006.01) |
| A61L 27/14 | (2006.01) |
| A61L 27/22 | (2006.01) |
| A61L 27/24 | (2006.01) |

(52) U.S. Cl.
CPC ........... *A61L 27/222* (2013.01); *A61L 27/507* (2013.01); *A61L 27/54* (2013.01); *A61L 27/58* (2013.01); *D01D 5/0076* (2013.01); *D01D 5/0084* (2013.01); *D01F 11/04* (2013.01); *A61L 27/225* (2013.01); *A61L 27/24* (2013.01); *D01D 5/0007* (2013.01)

(58) Field of Classification Search
CPC ........ A61L 27/14; A61L 27/18; A61L 27/507; A61L 27/54; A61L 27/56; A61L 27/58; A61L 2420/00; A61L 2430/00; A61L 2430/22; A61L 2240/0036; A61L 2430/36
See application file for complete search history.

(56) References Cited

U.S. PATENT DOCUMENTS

| | | | |
|---|---|---|---|
| 9,938,373 | B2 | 4/2018 | Wang et al. |
| 2003/0045927 | A1 | 3/2003 | Zilla et al. |
| 2005/0233062 | A1 | 10/2005 | Hossainy et al. |
| 2006/0009839 | A1 | 1/2006 | Tan |
| 2006/0020328 | A1 | 1/2006 | Tan |
| 2006/0085063 | A1 | 4/2006 | Shastri |
| 2007/0128171 | A1 | 6/2007 | Tranquillo et al. |
| 2007/0232169 | A1 | 10/2007 | Strickler et al. |
| 2008/0112998 | A1 | 5/2008 | Wang |
| 2008/0260798 | A1 | 10/2008 | Freyman et al. |
| 2009/0011486 | A1 | 1/2009 | Bettinger et al. |
| 2009/0012607 | A1 | 1/2009 | Kim et al. |
| 2009/0221047 | A1 | 9/2009 | Schindler et al. |
| 2010/0055184 | A1 | 3/2010 | Zeitels et al. |
| 2010/0233115 | A1 | 9/2010 | Petel et al. |
| 2011/0031656 | A1* | 2/2011 | Anneaux ................. A61L 31/06 264/484 |
| 2011/0236974 | A1 | 9/2011 | Ogle et al. |
| 2012/0271405 | A1* | 10/2012 | Soletti .................... A61B 17/11 623/1.15 |
| 2014/0079759 | A1 | 3/2014 | Patel et al. |
| 2014/0309726 | A1 | 10/2014 | Wang |
| 2015/0094797 | A1 | 4/2015 | Matheny |
| 2015/0238306 | A1* | 8/2015 | Marshall ............... A61F 2/0077 623/1.39 |
| 2015/0272729 | A1 | 10/2015 | Wagner et al. |
| 2015/0322202 | A1 | 11/2015 | Wang et al. |
| 2016/0355951 | A1* | 12/2016 | Pham ........................ D01F 8/02 |
| 2017/0072105 | A1 | 3/2017 | Jeffries et al. |
| 2018/0251596 | A1 | 9/2018 | Wang et al. |

FOREIGN PATENT DOCUMENTS

| | | |
|---|---|---|
| WO | WO 2013/154612 | 10/2013 |
| WO | WO-2013154612 A2 * | 10/2013 |

OTHER PUBLICATIONS

Extended European Search Report issued for EPC Application No. 16812399.0 dated Jan. 18, 2019.
Laktionov et al., "Electrospun produced small diameter vascular grafts: modification of physical properties and assessment of biocompatibility," *European Journal of Vascular and Endovascular Surgery*, (47)6): 692, Jun. 2014 (abstract only).
Melchiorri et al., "Development and assessment of a biodegradable solvent cast polyester fabric small-diameter vascular graft," *J Biomed Mater Res A*, 102(6): 1972-1981, Jun. 2014.
Allen et al., "Nerve regeneration and elastin formation within poly(glycerol sebacate)-based synthetic arterial grafts one-year post-implantation in a rat model," *Biomaterials*, 35(1): 165-173, Jan. 2014.
Amoabediny et al., "The role of biodegradable engineered scaffold in tissue engineering," *Biomaterials Science and Engineering*, ed. Pignatello, pp. 153-172, published online Sep. 15, 2011.
International Search Report and Written Opinion issued in International Application No. PCT/US2012/071389 dated Nov. 19, 2013.
Office Action from the United States Patent & Trademark Office in U.S. Appl. No. 14/365,987, dated Jan. 23, 2019.
"Substantial expression of mature elastin in arterial constructs," *PNAS*, 108(7): 2705-2710, Feb. 15, 2011.
Wang et al., "A tough biodegradable elastomer," *Nature Biotechnology*, vol. 20, pp. 602-606, Jun. 2002.
Allen et al., "Nerve regeneration and elastin formation within poly(glycerol sebacate)-based synthetic arterial grafts one-year post-implantation in a rat model," *Biomaterials*, 35(1): 167-173, Jan. 2014.
Amoabediny et al., "The role of biodegradable engineered scaffold in tissue engineering," *Biomaterials Science and Engineering*, pp. 153-172, Sep. 15, 2011.
Ifkovits et al., Biodegradable Fibrous Scaffolds with Tunable Properties Formed from Photocrosslinkable Poly(glycerol sebacate), *ACS Appl Mater Interfaces*, 1(9): 1878-1892, Sep. 30, 2009.
International Search Report and Written Opinion issued for International Application No. PCT/US2016/037790 dated Nov. 2, 2016.
International Search Report and Written Opinion issued for International Application No. PCT/US2012/071389 dated Nov. 19, 2013.
Kenar et al., "Design of a 3D aligned myocardial tissue construct from biodegradable polyesters," *J Mater Sci: Mater Med*, vol. 21, pp. 989-997, Oct. 29, 2009.
Lee et al., "Substantial expression of mature elastin in arterial constructs," *PNAS*, 108(7): 2705-2710, Feb. 15, 2011.
Non-Final Office Action dated for U.S. Appl. No. 14/365,987 dated May 9, 2017.
Non-Final Office Action issued for U.S. Appl. No. 14/652,744 dated Jul. 19, 2017.
Roh et al., "Tissue-engineered vascular grafts transform into mature blood vessels via an inflammation-mediated process of vascular remodeling," *PNAS*, 107(10): 4669-4674, Mar. 9, 2010.
Sant et al., "Hybrid PGS-PCL Microfibrous Scaffolds with Improved Mechanical and Biological Properties," *J Tissue Eng Regen Med.*, 5(4): 283-291, Apr. 2011.
Stowell et al., "Bioinductive vascular graft with clinically relevant dimensions and surgical handling," Poster presented at American Heart Association 23rd Annual Fellows Research Day, Jan. 23, 2015.
Stowell et al., "Fast-resorbing vascular grafts with robust surgical handling and clinically relevant dimensions," Poster presented at 14th Annual McGowan Institute for Regenerative Medicine Scientific Retreat, Mar. 8-10, 2015.
Tara et al., "Evaluation of remodeling process in small-diameter cell-free tissue-engineered arterial graft," *J. Vasc. Surg.*, 62(3): 734-743, Jan. 9, 2014.
Wang et al., "A tough biodegradable elastomer," *Nature Biotechnology*, vol. 20, pp. 602-606, Jun. 1, 2002.
Wu et al., "Fast Degrading Elastomer Enables Rapid Remodeling of a Cell-Free Synthetic Graft into a Neo-Artery," *Nature Medicine*, 18(7): 1148-1153, Jul. 2012.
Final Office Action issued for U.S. Appl. No. 14/365,987 dated Sep. 25, 2019.

(56) References Cited

OTHER PUBLICATIONS

Non-Final Office Action issued for U.S. Appl. No. 15/904,863 dated Oct. 10, 2019.
Yi et al., "Poly(glycerol sebacate) nanofiber scaffolds by core/shell electrospinning," *Macromol. Biosci.*, 8(9): 803-806, Sep. 9, 2008.

* cited by examiner

PCL Sheath Top View

FIG. 2B

PGS Core Cross-section

FIG. 2E

Top view of PGS core (uncoated)

FIG. 2A

Composite graft cross-section

FIG. 2D

Top view of finished graft

BIODEGRADABLE VASCULAR GRAFTS

CROSS REFERENCE TO RELATED APPLICATIONS

This application is the U.S. National Stage of International Application No. PCT/US2016/037790, filed Jun. 16, 2016, which was published in English under PCT Article 21(2), which in turns claims the benefit of U.S. Provisional Application No. 62/182,331, filed Jun. 19, 2015, which is herein incorporated by reference in its entirety.

ACKNOWLEDGMENT OF GOVERNMENT SUPPORT

This invention was made with government support under grants HL089658, 1S10RR02738301, and 2T32-HL076124 awarded by U.S. National Institutes of Health and grants 1247842 and 1359308 awarded by the National Science Foundation. The government has certain rights in the invention.

BACKGROUND

Small-diameter arterial substitutes are urgently needed as incidences of atherosclerotic arterial disease, especially coronary artery disease, rises with an aging population and increasing obesity. Autologous vessels are commonly used for bypass surgery to replace diseased and damaged arteries with an inner diameter less than 6 mm. However, autografts have several limitations including low availability, donor site morbidity, compliance mismatch, and late intimal hyperplasia, which often cause graft failure. Tissue engineering is an alternative to autografts with the potential to develop small-diameter arterial constructs that are nonthrombogenic, strong, and compliant. Yet, neither synthetic nor tissue-engineered grafts have yet to show clinical effectiveness in arteries smaller than 6 mm. Therefore, a need exists for small-diameter arterial substitutes that are nonthrombogenic, strong and compliant, but are effective in arteries less than 6 mm.

SUMMARY

Disclosed herein is a vascular graft, comprising a biodegradable scaffold comprising:
a biodegradable polyester electrospun tubular core;
a biodegradable polyester outer sheath surrounding the biodegradable polyester tubular core; and
a biodegradable poly(lactide) copolymer adhesive composition (i) disposed between the polyester electrospun tubular core and the polyester outer sheath, (ii) disposed between the polyester electrospun tubular core and the polyester outer sheath and on an outer surface of the polyester outer sheath, (iii) or disposed on an outer surface of the polyester outer sheath.

Also disclosed herein is a method of fabricating a vascular graft, comprising:
preparing a biodegradable polyester electrospun tubular core;
applying an adhesive composition comprising poly(lactide) copolymer to an outer surface of the biodegradable polyester electrospun tubular core; and
surrounding the adhesive-applied biodegradable polyester electrospun tubular core with a polyester sheath.

The foregoing will become more apparent from the following detailed description, which proceeds with reference to the accompanying figures.

BRIEF DESCRIPTION OF THE DRAWINGS

FIGS. 2A-2E are microphotographs showing the microstructure of an example of a scaffold.

DETAILED DESCRIPTION

I. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example." Although methods and materials similar or equivalent to those described herein can be used in the practice or testing of this disclosure, suitable methods and materials are described below. In addition, the materials, methods, and examples are illustrative only and not intended to be limiting.

In order to facilitate review of the various embodiments of this disclosure, the following explanations of specific terms are provided:

Anticoagulant: A substance that prevents the clotting of blood (coagulation). Anticoagulants are commonly administered to subjects to prevent or treat thrombosis. Generally, anticoagulants are administered to treat or prevent deep vein thrombosis, pulmonary embolism, myocardial infarction, stroke, and complications of mechanical prosthetic heart valves. Various types of anticoagulants with different mechanisms of action are available including anticoagulants that inhibit the effect of vitamin K (such as coumadin) or thrombin directly (such as argatroban, lepirudin, bivalirudin, and ximelagatran) or that activate antithrombin II that in turn blocks thrombin from clotting blood (such as heparin and derivative substances thereof).

Biocompatible: A term describing something that can be substantially non-toxic in the in vivo environment of its intended use, and is not substantially rejected by the patient's physiological system (e.g., is nonantigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of subjects, will not cause a significantly adverse reaction or response. Furthermore, biocompatibility can be affected by other contaminants such as prions, surfactants, oligonucleotides, and other agents or contaminants The term "biocompatible material" refers to a material that does not cause toxic or injurious effects on a tissue, organ, or graft.

Biodegradable polymer: A polymer that can be cleaved either enzymatically or hydrolytically to break it down sufficiently so as to allow the body to absorb or clear it away. A biodegradable graft is a graft in which at least a significant portion (such as at least 50%) of the graft degrades within one year of implantation.

Cell-free graft: A graft which does not contain cells, such as, endothelial or smooth muscle cells at the time of implantation.

Coat: As used herein "coating", "coatings", "coated" and "coat" are forms of the same term defining material and process for making a material where a first substance or substrate surface is at least partially covered or associated with a second substance. Both the first and second substance are not required to be different. Further, when a surface is "coated" as used herein, the coating may be effectuated by any chemical or mechanical bond or force, including linking agents. The "coating" need not be complete or cover the entire surface of the first substance to be "coated". The "coating" may be complete as well (e.g., approximately covering the entire first substance). There can be multiple coatings and multiple substances within each coating. The coating may vary in thickness or the coating thickness may be substantially uniform. Coatings contemplated in accordance with the present disclosure include, but not limited to medicated coatings, drug-eluting coatings, drugs or other compounds, pharmaceutically acceptable carriers and combinations thereof, or any other organic, inorganic or organic/inorganic hybrid materials. In an example, the coating is a thromboresistant coating which has anticoagulant properties, such as heparin.

Electroaerosoling: A process in which droplets are formed from a solution or melt by streaming an electrically charged polymer solution or melt through an orifice.

Electroprocessing: A process which includes any means of using an electrical field for depositing a material on a target.

Electrospinning: A process in which fibers are formed from a solution or melt by streaming an electrically charged solution or melt through an orifice.

Gelatin: A rapidly-degrading biocompatible material derived from collagen. Gelatin acts as a carrier for PGS to permit fiber formation by increasing fiber entanglement. Additionally, increased gelatin improves the morphology of fibers by reducing fiber fusion during electrospinning and heat curing. Gelatin may also have benefits for promoting cell adhesion and does not need to be removed like other carrier polymers. The disclosed methods herein utilize gelatin as a natural carrier polymer.

Heat-resistant carrier polymer: A polymer with sufficiently high glass transition temperatures and/or melting temperatures such that they remain solid or semi-solid at temperatures of 100 to 150° C., such as PVA, PHB, PET, polydioxanone (PDO), or poly(lactic acid) (PLA).

Poly(caprolactone)(PCL): A biodegradable polyester with a low melting point of around 60° C. and a glass transition temperature of about −60° C. PCL is prepared by ring opening polymerization of ε-caprolactone using a catalyst such as stannous octoate. PCL is degraded by hydrolysis of its ester linkages in physiological conditions (such as in the human body) and can be used as an implantable biomaterial. In some example, PCL is used as a sheath around a PGS scaffold.

Polyethylene terephthalate (PET): A thermoplastic polymer resin of the polyester family used in synthetic fibers. PET is formed with polymerized units of the monomer ethylene terephthalate, with repeating $C_{10}H_8O_4$ units. Clinical grade PET is an FDA approved material for vascular grafts. In some examples, PET is used as a carrier polymer in the disclosed methods and is blended with PGS.

Poly(glycerol sebacate)(PGS): An elastomeric biodegradable polyester. In some examples, a disclosed vascular graft includes a PGS scaffold.

Scaffold: A structural support facilitating cell infiltration and attachment in order to guide vessel growth. As disclosed herein, a biodegradable scaffold can be used to form a vascular graft. In some examples, a biodegradable scaffold includes a biodegradable polyester tubular core and a biodegradable polyester electrospun outer sheath surrounding the biodegradable polyester tubular core.

Sheath: An outer coating surrounding either partially or completely an inner layer. As disclosed herein, a sheath surrounds either partially or completely the biodegradable polyester tubular core of a disclosed vascular graft.

Subject: Living multi-cellular vertebrate organisms, a category that includes human and non-human mammals (such as laboratory or veterinary subjects). In an example, a subject is a human. In an additional example, a subject is selected that is in need of an implant for damaged or defective neo-artery.

Vascular graft: A tubular member which acts as an artificial vessel. A vascular graft can include a single material, a blend of materials, a weave, a laminate or a composite of two or more materials.

II. Biodegradable Scaffolds

Disclosed herein are scaffolds, such as tissue engineering scaffolds, including for the replacement and/or repair of damaged native tissues. Although the present disclosure illustrates in detail the use of a disclosed scaffold within a vascular graft, it is contemplated that a disclosed scaffold can be utilized for additional in situ tissue engineering applications, including, but not limited to bone, intestine, liver, lung, or any tissue with sufficient progenitor/stem cells. In certain embodiments, the disclosed scaffold could be used in a heart valve. In some examples, a scaffold is biodegradable and/or biocompatible and includes a biodegradable core, such as a biodegradable polyester tubular core for a vascular graft.

The present disclosure discusses in detail the fabrication methods for tubular vascular grafts. However, it is contemplated that the disclosed vascular grafts could also be fashioned with branches or bifurcations. In some examples, the branched vascular grafts may be formed by anastomosing two or more finished vascular grafts fabricated as tubes. In some examples, the branched vascular grafts may be fabricated in a single piece using the processes described herein.

In some examples, the biodegradable polyester tubular core includes PGS. In some examples, the biodegradable polyester tubular core includes PGS and one or more biodegradable substances similar to PGS, such as a polymer or an elastomer with relatively fast degradation rate (as described in detail below). These may include derivatives of polyglycolic acid, polycarbonate, polyurethane, polyethylene glycol, and poly(orthoester). It is contemplated that a disclosed graft may include PGS or any biodegradable and/or biocompatible substance with similar degradation rates and elasticity of PGS. In some examples, a disclosed scaffold includes PGS and/or one or more of the following polymers: polylactides (PLAs), poly(lactide-co-glycolides) (PLGAs), poly(dioxanone), polyphosphazenes, polyphosphoesters (such as, poly[1,4-bis(hydroxyethyl)terephthalate-alt-ethyloxyphosphate]; poly[1,4-bis(hydroxyethyl)terephthalate-alt-ethyloxyphosphate]-co-1,4-bis(hydroxyethyl)terephthalate-co-terephthalate; poly[(lactide-co-ethylene glycol)-co-ethyloxyphosphate]); polycaprolactone; poly(urethanes), polyglycolides (PGA), polyanhydrides, and polyorthoesters or any other similar synthetic polymers that may be developed that are biologically compatible. The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated by reference as if set forth fully herein.

In some embodiments, grafts, such as vascular grafts, which are biodegradable and/or biocompatible are disclosed. For example, a vascular graft can include a disclosed biodegradable scaffold with a biodegradable polyester core, such as a biodegradable polyester tubular core for a vascular graft. In some examples, the biodegradable polyester tubular core includes PGS. In some examples, the biodegradable polyester tubular core includes PGS and one or more biodegradable substances similar to PGS, such as a polymer or an elastomer with relatively fast degradation rate (as disclosed herein). These may include derivatives of polyglycolic acid, polycarbonate, polyurethane, polyethylene glycol, and poly(orthoester).

In some examples, a disclosed scaffold/graft includes one or more natural polymers including, but are not limited to amino acids, peptides, denatured peptides such as gelatin from denatured collagen, polypeptides, proteins, carbohydrates, lipids, nucleic acids, glycoproteins, minerals, lipoproteins, glycolipids, glycosaminoglycans, and proteoglycans. In certain embodiments, collagen is included. In certain embodiments, collagen is excluded. In certain cases, non-living macromolecular structures derived from biological tissues including, but are not limited to skins, vessels, intestines, internal organs, can be used alone or in combination with synthetic polymers named above.

In some examples, the scaffold core or graft core includes pores to facilitate cell infiltration, but pores are not necessarily required. In examples in which pores are built into the scaffolds or grafts, the pore size can range from 2 to 500 microns (μm). In some examples, the biodegradable polyester core, such as a biodegradable polyester tubular core, comprises pores of about 1 μm to about 500 μm, from about 10 μm to about 400 μm, about 20 μm to about 300 μm, about 1 μm to about 10 μm, about 3 μm to about 7 μm, such as 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 30 μm, 40 μm, 50 μm, 60 μm, 70 μm, 80 μm, 90 μm, 100 μm, 150 μm, 200 μm, 250 μm, 300 μm, 350 μm, 400 μm, 450 μm, or 500 μm. In some examples, pores are about 20 μm to about 30 μm, including about 20 μm, 21 μm, 22 μm, 23 μm, 24 μm, 25 μm, 26 μm, 27 μm, 28 μm, 29 μm, and 30 μm. In some examples, the pores are uniformly distributed. In some examples, the pores are non-uniformly distributed. In some examples, the biodegradable polyester tubular porous core has at least 75% pore interconnectivity, such as about 80% to about 90%, about 90% to about 98%, including 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% interconnectivity.

In some examples, the biodegradable scaffold further includes a sheath which surrounds the biodegradable polyester tubular core. In some examples, the sheath is a biodegradable polyester electrospun sheath which surrounds the biodegradable polyester tubular core to prevent, inhibit or reduce bleeding from such graft. In some examples, the biodegradable polyester electrospun sheath includes PCL or a PCL like substance which is capable of forming a leak-proof sheath around the biodegradable polyester electrospun sheath. The capability of a sheath to prevent leakage may be enhanced by infiltration of the sheath structure by an adhesive as described in more detail below.

In one particular example, the biodegradable scaffold includes a PGS core surrounded by an electrospun PCL sheath, and a biodegradable poly(lactide-co-caprolactone) material disposed between the PGS core and the electrospun PCL sheath.

In some examples, the sheath has a thickness between about 5 μm and 30 μm, such as between about 10 μm, and about 20 μm, including 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, and 30 μm. In one example, the biodegradable polyester electrospun outer sheath has a thickness of about 15 μm.

In some examples, the sheath has a thickness between about 50 μm and 175 μm, such as between about 75 μm and about 150 μm, including 75 μm, 80 μm, 85 μm, 90 μm, 95 μm, 100 μm, 105 μm, 110 μm, 115 μm, 120 μm, 125 μm, 130 μm, 135 μm, 140 μm, 145 μm, or 150 μm. In one example, the biodegradable polyester electrospun outer sheath has a thickness of about 125 μm. In some examples, the sheath thickness is uniform over the graft length. In some examples, the sheath thickness varies over the graft length.

In some examples, the sheath has a thickness between about 200 μm and 800 μm, such as between about 200 μm and about 400 μm, about 400 μm and about 600 μm, and about 600 μm and about 800 μm, including 200 μm, 250 μm, 300 μm, 350 μm, 400 μm, 450 μm, 500 μm, 550 μm, 600 μm, 650 μm, 700 μm, and 800 μm. In one example, the biodegradable polyester electrospun outer sheath has a thickness of about 600 μm. In some examples, the sheath thickness is uniform over the graft length. In some examples, the sheath thickness varies over the graft length.

In some examples, the biodegradable scaffold is coated with a biocompatible and/or biodegradable material. In some examples, the inner luminal surface of the biodegradable scaffold is coated with a biocompatible and/or biodegradable material. It is contemplated that such coating may be complete or partial. In some examples, the inner luminal surface of a biodegradable scaffold is coated completely with a thromboresistant agent, such as heparin and/or other compounds known to one of skill in the art to have similar anti-coagulant properties as heparin, to prevent, inhibit or reduce clotting within the inner lumen of the vascular graft.

In some examples, the scaffold can be impregnated with any of a variety of agents, such as, for example, suitable growth factors, stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), hepatocyte growth factor (HGF), stromal cell derived factor (SDF), platelet derived growth factor (PDGF), keratinocyte growth factor (KGF), skeletal growth factor (SGF), osteoblast-derived growth factor (BDGF), insulin-like growth factor (IGF), cytokine growth factor (CGF), stem cell factor (SCF), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), interferon, interleukins, cytokines, integrin, collagen, elastin, fibrillins, fibronectin, laminin, glycosaminoglycans, heparan sulfate, chondrotin sulfate (CS), hyaluronic acid (HA), vitronectin, proteoglycans, transferrin, cytotactin, tenascin, and lymphokines.

The various dimensions of a disclosed scaffold or graft may vary according to the desired use. In principle, the dimensions will be similar to those of the host tissue in which the scaffold/graft is being used to replace. For examples, the inner diameter of a vascular graft will match that of the host vessel to be replaced. In some examples, the inner diameter is between about 0.5 mm to 25 mm. In some examples, the inner diameter of a disclosed vascular graft is 4 to 7 mm (e.g., peripheral bypass). In some examples, the inner diameter of a disclosed vascular graft is 10to 25 mm (e.g., great vessels). In some examples, the inner diameter is between about 1 mm to 5 mm. In some examples, a disclosed vascular graft has an inner diameter of between about 700 to about 5000 μm, such as about 710 μm to about 4000 μm, such as about 720 μm to about 3000 μm, such as about 1000 μm to about 5000 μm, including 710 μm, 711 μm, 712 μm, 713 μm, 714 μm, 715 μm, 716 μm, 717 μm, 718 μm, 719 μm, 720 μm, 721 μm, 722 μm, 723 μm, 724 μm, 725 μm, 726 μm, 727 μm, 728 μm, 729 μm, 730 μm, 731 μm, 732 μm, 733 μm, 734 μm, 735 μm, 736 μm, 737 μm, 738 μm, 739 μm, 740 μm, 741 μm, 742 μm, 743 μm, 744 μm, 745 μm, 746 μm, 747 μm, 748 μm, 749 μm, 750 μm, 800 μm, 850 μm, 900 μm, 950 μm, 1000 μm, 2000 μm, 3000 μm, 4000 μm or 5000 μm. In some examples, the inner diameter of a disclosed vascular graft is about 720 μm. In some examples, the inner diameter of a disclosed vascular graft is about 1000 μm. In some examples, the inner diameter of a disclosed vascular graft is about 2000 μm. In some examples, the inner diameter of a disclosed vascular graft is about 3000 μm.

Typically, the wall thickness of a disclosed scaffold or vascular graft is designed to match that of the host tissue or vessel to be replaced. However, it is contemplated the graft can be thicker or thinner, if desired. In some examples, a disclosed vascular graft has a wall thickness between about 500 μm and about 1000 μm. In some examples, a disclosed vascular graft has a wall thickness between about 2000 μm and about 4000 μm. In some examples, a disclosed vascular graft has a wall thickness between about 100 μm and about 500 μm, such as about 150 μm and about 450 μm, including about 200 μm and about 400 μm, such as about 100 μm, 125 μm, 150 μm, 175 μm, 200 μm, 225 μm, 250 μm, 275 μm, 300 μm, 325 μm, 350 μm, 375 μm, 400 μm, 425 μm, 450 μm, 475 μm, or 500 μm. In some examples, a disclosed vascular graft has a wall thickness between about 270 μm and about 300 μm, such as about 285 μm and about 295 μm, including 270 μm, 271 μm, 272 μm, 273 μm, 274 μm, 275 μm, 276 μm, 277 μm, 278 μm, 279 μm, 280 μm, 281 μm, 282 μm, 283 μm, 284 μm, 285 μm, 286 μm, 287 μm, 288 μm, 289 μm, 290 μm, 291 μm, 292 μm, 293 μm, 294 μm, 295 μm, 296 μm, 297 μm, 298 μm, 299 μm, or 300 μm. In some examples, the wall thickness is about 290 μm.

In certain embodiments, the scaffold/graft has a length of at least 1, more particularly at least 5, and most particularly at least 10, cm. In certain embodiments, the scaffold/graft has a length of ≤150, more particularly 130, and most particularly 110, cm.

In some examples, at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of a disclosed scaffold/graft, such as a disclosed vascular graft, degrades within one year of implantation, such as within 1 to 10 months, including within 1 month, 2 months, 3 months, 4 months, 5 months, 6 months, 7 months, 8 months, 9 months, 10 months, 11 months or 12 months of implantation. In some examples, at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of a disclosed scaffold/graft, such as a disclosed vascular graft, degrades within 2 weeks to 52 weeks of implantation, including within 4 weeks, 6 weeks, 8 weeks, 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, or 52 weeks of implantation.

In some examples, about 80% to about 95% of the graft degrades within 4 weeks. In some examples, about 80% to about 95% of the graft degrades within 6 weeks. In some examples, about 80% to about 95% of the graft degrades within 8 weeks. In some examples, about 80% to about 95% of the graft degrades within 10 weeks. In some examples, about 80% to about 95% of the graft degrades within 14 weeks. In some examples, about 80% to about 95% of the graft degrades within 16 weeks. In some examples, about 80% to about 95% of the graft degrades within 18 weeks. In some examples, about 80% to about 95% of the graft degrades within 20 weeks. In some examples, about 80% to about 95% of the graft degrades within 22 weeks. In some examples, about 80% to about 95% of the graft degrades within 24 weeks. In some examples, about 80% to about 95% of the graft degrades within 26 weeks.

In some examples, at least 90% of the graft degrades within 4 weeks. In some examples, at least 90% of the graft degrades within 6 weeks. In some examples, at least 90% of the graft degrades within 8 weeks. In some examples, at least 90% of the graft degrades within 10 weeks. In some examples, at least 90% of the graft degrades within 12 weeks. In some examples, at least 90% of the graft degrades within 14 weeks. In some examples, at least 90% of the graft degrades within 16 weeks. In some examples, at least 90% of the graft degrades within 18 weeks. In some examples, at least 90% of the graft degrades within 20 weeks. In some examples, at least 90% of the graft degrades within 22 weeks. In some examples, at least 90% of the graft degrades within 24 weeks. In some examples, at least 90% of the graft degrades within 26 weeks.

In some examples, at least 95% of the graft degrades within 4 weeks. In some examples, at least 95% of the graft degrades within 6 weeks. In some examples, at least 95% of the graft degrades within 8 weeks. In some examples, at least 95% of the graft degrades within 10 weeks. In some examples, at least 95% of the graft degrades within 12 weeks. In some examples, at least 95% of the graft degrades within 14 weeks. In some examples, at least 95% of the graft degrades within 16 weeks. In some examples, at least 95% of the graft degrades within 18 weeks. In some examples, at least 95% of the graft degrades within 20 weeks. In some examples, at least 95% of the graft degrades within 22 weeks. In some examples, at least 95% of the graft degrades within 24 weeks. In some examples, at least 95% of the graft degrades within 26 weeks.

In some examples, at least 50%, such as about 55% to about 70%, about 80% to about 90%, about 90% to about 98%, including 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% of a disclosed scaffold/graft, such as a disclosed vascular graft, degrades within 4 weeks of implantation, such as within 1 week, 2 weeks, 3 weeks and 4 weeks.

In some examples, a disclosed scaffold/graft, such as a disclosed vascular graft, is cell-free, in which it does not include any living cells, such as smooth muscle cells or endothelial cells.

Disclosed herein is a scaffold that includes an adhesive in contact with the sheath. In certain embodiments, the adhesive is disposed only between the core and the sheath. In other embodiments, the adhesive is disposed between the core and the sheath and is disposed on the outer surface of the sheath, particularly for embodiments with thicker sheaths (for example, 100 to 150 µm). Applying the adhesive to both the outer surface of the core and the outer surface of the sheath means that the adhesive can penetrate the sheath from both surfaces of the sheath. Adhesive penetration of the full thickness of the sheath improves adhesion and prevents the sheath from delaminating internally. In further embodiments, the adhesive is disposed only on the outer surface of the sheath. In certain embodiments, a discrete layer of adhesive between the core and the sheath may be not be present because the full amount of the adhesive has diffused into the sheath, into the core, or into both the sheath and the core, but the adhesive is still considered to be "disposed" between the core and the sheath. Similarly, a discrete layer of adhesive may be not be present on the outer surface of the sheath because the full amount of the adhesive has diffused into the sheath, but the adhesive is still considered to be "disposed" on the outer surface of the sheath.

In certain embodiments, the adhesive meets one, or a combination of more than one, of the following criteria:

A biodegradable rate that is between the biodegradable rate of the core and the biodegradable rate of the sheath. In certain embodiments, the biodegradable rate of the adhesive is about 2% to about 20% of the original mass per week, including 2%, 3%, 4%, 5%, 6%, 7%, 8%, 9%, 10%, 11%, 12%, or 13% of the original mass per week. In certain embodiments, the biodegradable rate of the PGS core is about 10% to about 25% of the original mass per week, the biodegradable rate of the adhesive is about 5% to about 20% of the original mass per week, and the biodegradable rate of the PCL sheath is about 5% to about 15% of the original mass per month.

A stiffness and elasticity that enables the scaffold to serve as a vascular graft. For example, the adhesive may have an elastic modulus of about 100 kPa to about 10 MPa, including 100 kPa, 200 kPa, 300 kPa, 400 kPa, 500 kPa, 600 kPa, 700 kPa, 800 kPa, 900 kPa, 1 MPa, 2 MPa, 3 MPa, 4 MPa, 5 MPa, 6 MPa, 7 MPa, 8 MPa, 9 MPa, and 10 MPa. The adhesive may also have a strain recovery of at least 80% at 10% strain, such as at least 85% or at least 90%. In certain embodiments, the scaffold has an elasticity of at least 80% circumferentially as measured by residual deformation after 66 h of pressurization to 120 mmHg at 10% longitudinal extension. In certain embodiments, the scaffold has an elasticity of at least 90% longitudinally as measured by residual deformation after 66 h of pressurization to 120 mmHg at 10% longitudinal extension.

Biocompatibility.

Bond strength between the core and sheath that is sufficient so that the scaffold retains structural integrity as it is handled during implantation procedures. In particular, the adhesive may prevent delamination of the scaffold as it is handled and manipulated by medical personnel during implantation.

Figure 2A:
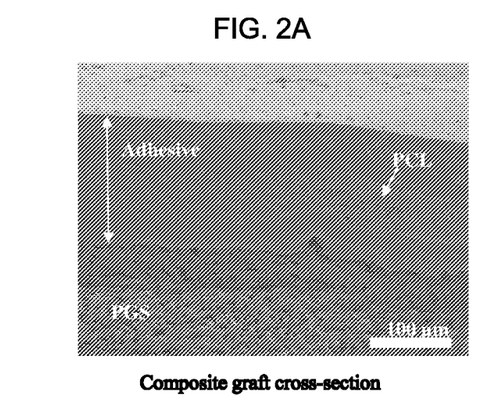
FIG. 2A shows a PGS core/PCL sheath interface, and penetration of the adhesive into a portion of the PCL sheath microstructure.
Figure 2B:
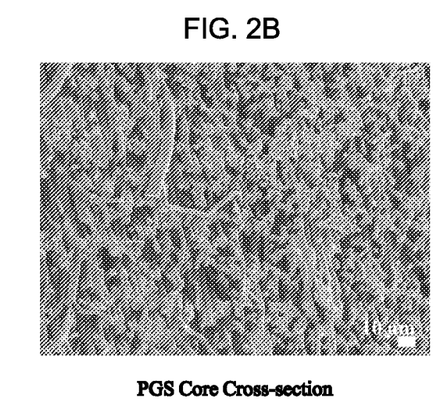
FIG. 2B shows a cross-section of a PGS core, which is porous with high pore interconnectivity.
Figure 2C:
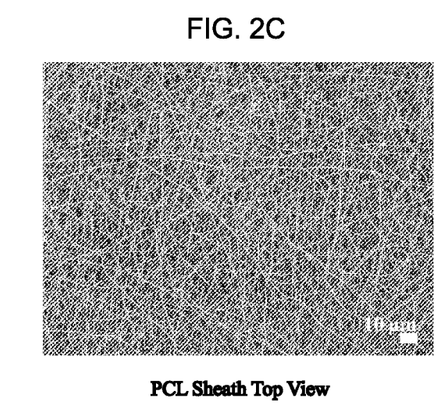
FIG. 2C shows a top view of a PCL sheath.
Figure 2D:
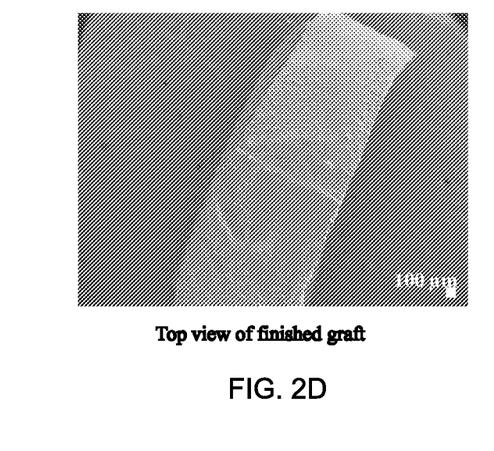
FIG. 2D shows a top view of a finished graft.
Figure 2E:
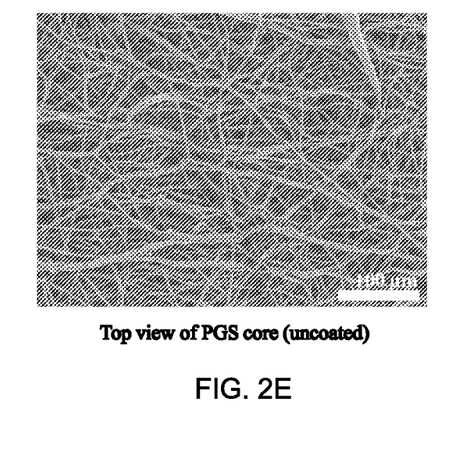
FIG. 2E shows a top view of an adhesive uncoated PGS core.

Sealant for sheath. In certain embodiments, the adhesive infiltrates at least a portion of the porous fibrous sheath material thereby enhancing the seal properties of the scaffold. However, the adhesive should not penetrate deeply into the core structure, to avoid compromising the porous structure of the core that facilitates cellular vascular remodeling. For example, the adhesive may penetrate into the sheath material for a distance of at least 20 µm, more particularly at least 50 µm, and most particularly at least 100 µm, µm from the core/sheath interface. FIG. 2A shows an example of the adhesive penetrating the sheath microstructure.

Nonporous

Suture retention and compressibility of the scaffold. Suture retention load may be up to 1.3 N, 1.5 N, or 2.0 N. When wet, the scaffold can fully recover its circular shape after compression—this is important for ease of implantation and for patient safety.

In certain embodiments, the adhesive includes a poly (lactide) copolymer. Illustrative poly(lactide) copolymers include poly(lactide-co-caprolactone), poly(D,L-lactide-co-caprolactone), poly(D,L-lactide-co-glycolide), poly(L-lactide-co-glycolide), and poly(L-lactide-co-caprolactone-co-glycolide. In certain embodiments, the poly(lactide-co-caprolactone) has a monomer ratio of lactide:caprolactone of 80:20, more particularly 65:35, most particularly 50:50. In certain embodiments, the poly(lactide-co-caprolactone) has a $M_n$ of 20,000 to 150,000, more particularly 30,000 to 100,000, and most particularly 75,000 to 80,000, daltons. In certain embodiments, the poly(lactide-co-caprolactone) has a melting point(s) of 50 to 180, more particularly 100 to 160, and most particularly 120 to 150, ° C. In certain embodiments, the poly(lactide-co-caprolactone) is amorphous and has no defined melting point. In certain embodiments, the poly(lactide-co-caprolactone) has a $T_G$ of −15 to 30, more particularly −10 to 20, and most particularly about −5, ° C. In certain embodiments, the poly(lactide-co-caprolactone) is poly(L-lactide-co-caprolactone), particularly poly(L-lactide-co-ε-caprolactone).

In certain embodiments, a synthetic or biologic additive may be included in the adhesive composition. For example, the synthetic may include poly(ε-caprolactone), poly(L-lactide), poly(D-lactide), poly(D,L-lactide), prepolymer poly(glycerol sebacate), poly(vinyl alcohol), poly(ethylene glycol), polyglycolide, or oligomers thereof. For example, the biologic may include silk fibroin, collagen, gelatin, fibrin, elastin, tropoelastin, heparin, or any of the growth factors previously listed as being impregnated into the scaffold as a whole.

III. Methods of Fabrication

Also disclosed herein are methods of fabricating a scaffold or graft, such as a vascular graft. A disclosed scaffold or graft may be fabricated by methods known to those of skill in the art. In some embodiments, a method of fabricating a scaffold or graft, such as a vascular graft, which is biodegradable and/or biocompatible comprises preparing a biodegradable polyester core (such as a tubular core for a vascular graft) and surrounding the biodegradable polyester core with a sheath. In some examples, a disclosed scaffold or graft is prepared by using salt fusion and leaching or electroprocessing, such as electrospinning. In particular examples, the method includes synthesizing the biodegradable polyester material and then forming a core, such as a tubular core, with such material. The biodegradable polyester material can be synthesized by any method known to one of skill in the art to generate the material with desired properties, including, but not limited to, a desired shape, thickness, porosity, fiber strength, or elasticity. For example, PGS can be first synthesized by any method known to one of ordinary skill in the art, including, but not limited to, the method described in Wang et al. (*Nat. Biotechnol.* 20:602-606, 2002) which is hereby incorporated by reference in its entirety). The synthesized biocompatible and biodegradable polyester material can then formed into the desired shape by use of any method known to one of ordinary skill in the art. In some examples, the biodegradable and biocompatible polyester material is shaped based upon the shape of the structure, such as a blood vessel, the resulting vascular graft is replacing. In some examples, a PGS tube is formed by the method described in Lee et al. (*Proc Natl Acad Sci USA* 108: 2705-2710, 2011) which is hereby incorporated by reference in its entirety except that a 1 mm mandrel and a 1.25 mm outer mold is used.

In some examples, the biodegradable core, such as tubular core, is fabricated to comprise pores of about 1 µm to about 500 µm, from about 10 µm to about 300 about 20 µm to about 300 µm, about 1 µm to about 10 µm, about 3 µm to about 7 µm, such as 1 µm, 2 µm, µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, or 500 µm. In some examples, pores are about 20 µm to about 30 µm, including about 20 µm, 21 µm, 22 µm, 23 µm, 24 µm, 25 µm, 26 µm, 27 µm, 29 µm, and 30 µm. In some examples, the biodegradable core is fabricated to include uniformly distributed pores. In some examples, the biodegradable polyester core is fabricated to include non-uniformly distributed pores. In some examples, the biodegradable polyester tubular porous core is fabricated to include at least 75% pore interconnectivity, such as about 80% to about 90%, about 90% to about 98%, including 75%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.99% interconnectivity.

In certain embodiments, the core is fabricated by electrospinning PGS. In particular, disclosed herein are methods of electrospinning PGS which overcome the limitations associated with the previous methods of electrospinning. The disclosed methods allow stable PGS fibers and fibrous PGS constructs, scaffolds and grafts to be formed. It is to be noted that inconsistencies exist in the nomenclature of PGS. In particular, previous publications which report electrospinning of PGS are in fact reporting the electrospinning of PGS prepolymer in a carrier polymer, not crosslinked PGS. Herein, the polymer before crosslinking is referred to as PGS prepolymer whereas the term "PGS" denotes cross-linked (cured) PGS.

In one example, a disclosed method includes generating PGS fibers, such as PGS micro- or nano-fibers by blending PGS prepolymer with a heat resistant natural or synthetic polymer carrier, including, but not limited to polyvinyl alcohol (PVA), polyhydroxybuytrate (PHB) or polyethylene terephthalate (PET), wherein the blend is electrospun into micro- or nano-fibers, and the PGS prepolymer is cross-linked into PGS with heat without using chemical cross-linkers. In these examples, standard electrospinning equipment and techniques are used and not core-shell electrospinning equipment and techniques. In some examples, the method further includes removing the heat-resistant "carrier polymer".

In one example, a disclosed method includes electrospinning PGS prepolymer and PVA, wherein electrospun PGS is cross-linked without using chemical cross-linkers; and the PVA is removed by washing with distilled water, thereby forming a PGS fibrous construct. In another example, a method of preparing a fibrous construct includes electrospinning PGS prepolymer and a natural carrier polymer, such as gelatin, wherein electrospun PGS is cross-linked with heat without using chemical cross-linkers, thereby forming a fibrous construct containing both PGS and the natural carrier, such as gelatin. Another example constructs a fibrous PGS construct by preparing an electrospinning precursor solution comprising blending PGS prepolymer with poly(lactic-co-glycolic acid) (PLGA) and a chemical cross-linker; electrospinning the prepared blend; and exposing the electrospun blend to an organic solvent to remove the PLGA. Also disclosed are compositions made therefrom, including fibrous constructs which can be used as scaffolds, such as tissue engineering scaffolds or cell-free implants, including for the replacement and/or repair of damaged native tissues.

In some embodiments, the PGS prepolymer and a carrier polymer (such as PVA, PHB, PET or a combination thereof) solution comprises PGS and a carrier polymer at a ratio of about 50:50; 45:55; 55:45; 40:60; or 60; 40, respectively.

In some embodiments of the method, heat curing comprises exposing electrospun PGS prepolymer and heat-resistant carrier polymer construct to between 7° C. and 20° C. temperature for between 2 weeks and 10 hours.

In some embodiments of the method, heat curing comprises exposing the electrospun PGS prepolymer and carrier polymer to 12° C. temperature for about 24 hours or 48 hours; or 150° C. for 24 hours; or 12° C. for 24 hours followed by 150° C. for 24 hours.

In some embodiments, a method of preparing a fibrous construct is disclosed comprising electrospinning a PGS prepolymer and gelatin solution, wherein the PGS prepolymer and gelatin is cross-linked with heat without using chemical cross-linkers, thereby preparing a fibrous construct.

In some embodiments, the method further comprises preparing a PGS and gelatin solution by combining PGS and gelatin with hexafluoroisopropanol (HFIP)-water prior to electrospinning In some embodiments, the PGS prepolymer and gelatin solution comprises PGS prepolymer and gelatin at a ratio of about 50:50.

In some embodiments of the method, heat curing comprises exposing the electrospun PGS prepolymer and gelatin to 13° C. temperature for about 24 hours.

In other embodiments, a method of preparing a fibrous construct is disclosed comprising preparing an electrospinning precursor solution comprising blending PGS prepolymer with poly(lactic-co-glycolic acid) (PLGA) and a chemical cross-linker; electrospinning the blended PGS prepolymer, PLGA and chemical cross-linker to form an electrospun PGS, PLGA, chemically cross-linked construct; and exposing the electrospun PGS, PLGA, chemically cross-linked construct to an organic solvent, thereby removing the PLGA and forming a PGS, chemically cross-linked construct.

In some embodiments of the method, the chemical cross-linker is lysine triisocyanate.

In some embodiments of the method, preparing an electrospinning precursor solution further comprises adding lithium bromide dissolved in tetrahydrofuran to the PGS prepolymer, PLGA and chemical cross-linker solution.

The adhesive may be applied to the outer surface of the core. The adhesive may be applied in any manner, for example, coating, spraying, dripping, dipping, electroaerosoling, or by being soaked into the sheath before the sheath is applied. The adhesive may cover substantially all of the outer surface area of the core, or only a portion of the outer surface area of the core. The adhesive may cover substantially all of the outer surface area of the outer sheath, or only a portion of the outer surface area of the outer sheath. In certain embodiments the core is placed on a holder (for example, a mandrel) for applying the adhesive to the core. The holder may be spun during application of the adhesive.

In certain embodiments, the adhesive is applied as a liquid. For example, the poly(lactide-co-caprolactone) may be dissolved in a solvent. In certain embodiments, the solvent for the poly(lactide-co-caprolactone) includes dichloromethane, acetone, or blends thereof. For example, the blended solvent volume ratio may be at least 1:1 parts dichloromethane:acetone, more particularly at least 3:7 parts, and most particularly 1:9 parts. For example, the polymer concentration in the solvent may be about 0.01-0.10 g per solvent added, such as about 0.01, 0.02, 0.03, 0.04, 0.05, 0.06, 0.07, 0.08, 0.09, or 0.10 g per ml solvent added. In one example, the adhesive solution composition is 0.025 g per 0.1 ml of dichloromethane and 0.9 ml of acetone. It was found that these solvent systems enable sufficient adhesive penetration into both the sheath and the core to provide a strong adhesive bond.

In some examples, only one coat of adhesive is applied. In some examples, multiple coats of adhesive are applied. Furthermore, in some examples, different coats have different solution compositions. In some examples, different coats have the same solution composition.

In certain embodiments, the adhesive is dried after it is applied to the outer surface of the core. For example, the adhesive may be dried by airflow, by spinning, by heating to less than the melting point of the PCL sheath or the PLCL, or by combinations thereof. In some embodiments, the open time of the adhesive is between 10 and 60 s, such as 10, 20, 30, 40, 50, or 60 s. In some embodiments, the working time of the adhesive is between 10 and 60 s, including 10, 20, 30, 40, 50, or 60 s.

The amount of adhesive applied to the outer surface of the core may vary. In certain embodiments the amount may be 50-1000 ul per $cm^2$, such as 50 ul, 100 ul, 150 ul, 200 ul, 250 ul, 300 ul, 400 ul, 500 ul, 600 ul, 700 ul, 800 ul, 900 ul, and 1000 ul.

In some examples, the sheath is fabricated to surround the biodegradable polyester core, such as tubular core, by electrospinning For example, a PCL sheath is formed around a PGS or like composition core by electrospinning PCL onto a PGS core. In one embodiment, a PCL sheath is electrospun onto another mold and subsequently transferred onto the PGS core. For example, the mold may be a tubular mandrel of diameter equal to or larger than the PGS core. For example, the mold may be a flat electrospinning collector. For example, the mold may be an electrospinning collector constructed with a gap such that a mat of fibers is suspended in the air between portions of the collector.

In some examples, the sheath is fabricated by weaving. In some examples, the sheath is fabricated by knitting, including tubular knitting. In some examples, the sheath is fabricated by braiding, including tubular braiding. In some examples, the sheath is fabricated by nonwoven textile processes, including meltblowing, spunbonding, dry laying, or wet laying.

In some examples, the sheath is fabricated as a seamless tube. In other examples, the sheath is fabricated as a flat mat that is subsequently wrapped around the PGS core to produce a seamed tube. In some examples, the adhesive holds the seam in place. In some examples, the seam is reinforced by fusing the fibers of the sheath at various locations, such as by point melting or point dissolution. In some examples, the seam is reinforced by a sewn line of suture, which may be continuous or interrupted. In some embodiments, a second line of reinforced points is fabricated 18° around the circumference from the seam.

In some examples, the sheath is fabricated to have a thickness between about 5 µm and 30 µm, such as between about 10 µm and about 20 µm, including 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, and 30 µm. In one example, the biodegradable polyester outer sheath has a thickness of about 15 µm.

In some examples, the sheath has a thickness between about 50 µm and 175 µm, such as between about 75 µm and about 150 µm, including 75 µm, 80 µm, 85 µm, 90 µm, 95 µm, 100 µm, 105 µm, 110 µm, 115 µm, 120 µm, 125 µm, 130 µm, 135 µm, 140 µm, 145 µm, or 150 µm. In one example, the biodegradable polyester outer sheath has a thickness of about 125 µm. In some examples, the sheath thickness is uniform over the graft length. In some examples, the sheath thickness varies over the graft length.

In some examples, the sheath has a thickness between about 200 µm and 800 µm, such as between about 200 µm and about 400 µm, about 400 µm and about 600 µm, and about 600 µm and 800 µm, including 200 µm, 250 µm, 300 µm, 350 µm, 400 µm, 450 µm, 500 µm, 550 µm, 600 µm, 650 µm, 700 µm, and 800 µm. In one example, the biodegradable polyester outer sheath has a thickness of about 600 µm. In some examples, the sheath thickness is uniform over the graft length. In some examples, the sheath thickness varies over the graft length.

In further examples, the disclosed methods of fabrication include coating a surface of the biodegradable scaffold, such as a surface of a biodegradable polyester tubular core with a biocompatible and/or biodegradable material. It is contemplated that one of ordinary skill in the art can determine with but limited experimentation, which substrates are suitable for a particular application. In some examples, the inner luminal surface of the biodegradable scaffold is coated with a biocompatible and/or biodegradable material. It is contemplated that such coating may be complete or partial. In some examples, the inner luminal surface of a biodegradable scaffold is coated completely with a thromboresistant agent, such as heparin and/or other compounds known to one of skill in the art to have similar anti-coagulant properties as heparin, to prevent, inhibit or reduce clotting within the inner lumen of the vascular graft.

The various dimensions of a disclosed graft may vary according to the desired use, and are described above in detail.

In some examples, the method of fabrication includes generating a cell-free scaffold/graft, such as a cell-free vascular graft, in which the graft does not include any living cells, such as smooth muscle cells or endothelial cells.

IV. Methods of Use

It is contemplated that the disclosed scaffolds/grafts can be used to guide host tissue remodeling in many different tissues, including any tissue that has progenitor cells. The disclosed biodegradable scaffolds can be used to facilitate tissue regeneration in vivo by providing a structural frame for which tissue regeneration can occur. In some examples, the scaffolds/grafts or constructed to allow and facilitate the infiltration of host cells including progenitor cells. In some examples, the scaffolds/graft allows and facilitates host remodeling of the biodegradable structure, so that eventually the polymeric structure is replaced by the desirable host tissue. It is contemplated that the methods of fabrication disclosed in Section III and the Example below can be modified as desired by one of ordinary skill in the art to fabricate a graft with the appropriate dimensions and features depending upon tissue which is to be replaced.

The disclosed scaffolds are especially useful for applications in soft and elastomeric tissues. In some particular examples, the generated tissue constructs are for the replacement and/or repair of damaged native tissues. For example, the disclosed constructs are contemplated to be implantable for tensile load bearing applications, such as being formed into tubes and implanted as artery interpositional grafts as well as other tensile load bearing applications. A disclosed scaffold/graft can be utilized for additional in situ tissue engineering applications, including, but not limited to bone, intestine, liver, lung, or any tissue with sufficient progenitor/stem cells. For example, uses can range from sheets for hernia repair, prolapse, and wound dressings, to complex tubes for blood vessel, nerve and trachea repair. Additionally, aligned random transition spinning may be useful for ligament-bone interfaces.

In some particular examples, a biodegradable scaffold comprising a biodegradable polyester core and a biodegradable polyester electrospun outer sheath surrounding the biodegradable polyester core with or without a thromboresistant agent coating the biodegradable scaffold is used to facilitate tissue regeneration in vivo by providing a structural frame for which tissue regeneration can occur.

In some examples, a disclosed vascular graft is used to form a blood vessel in vivo. For example, a disclosed vascular graft can be implanted into a subject in need of vascular graft at the desired location to form a conduit in which blood may initially flow and ultimately form a blood vessel, such as blood vessel of less than 30 mm inner diameter, such as less than 25 mm or less than 7 mm, including, about 25 mm, about 20 mm, about 15 mm, about 10 mm, about 9 mm, about 8 mm, about 7 mm, about 6 mm, about 5 mm, about 4 mm, about 3 mm, about 2 mm, or about 1 mm, or as low as 0.5 mm. In some examples, the vascular graft is used as a coronary or a peripheral arterial graft or venous grafts or lymphatic vessels. In some examples, the vascular graft is used as an arteriovenous shunt for dialysis access where "maturation" of 2-3 months is common.

In some examples, the vascular graft is used as an aortic graft or a graft for the great vessels of the heart.

The following examples are provided to illustrate certain particular features and/or embodiments. These examples should not be construed to limit the disclosure to the particular features or embodiments described.

Figure 1:
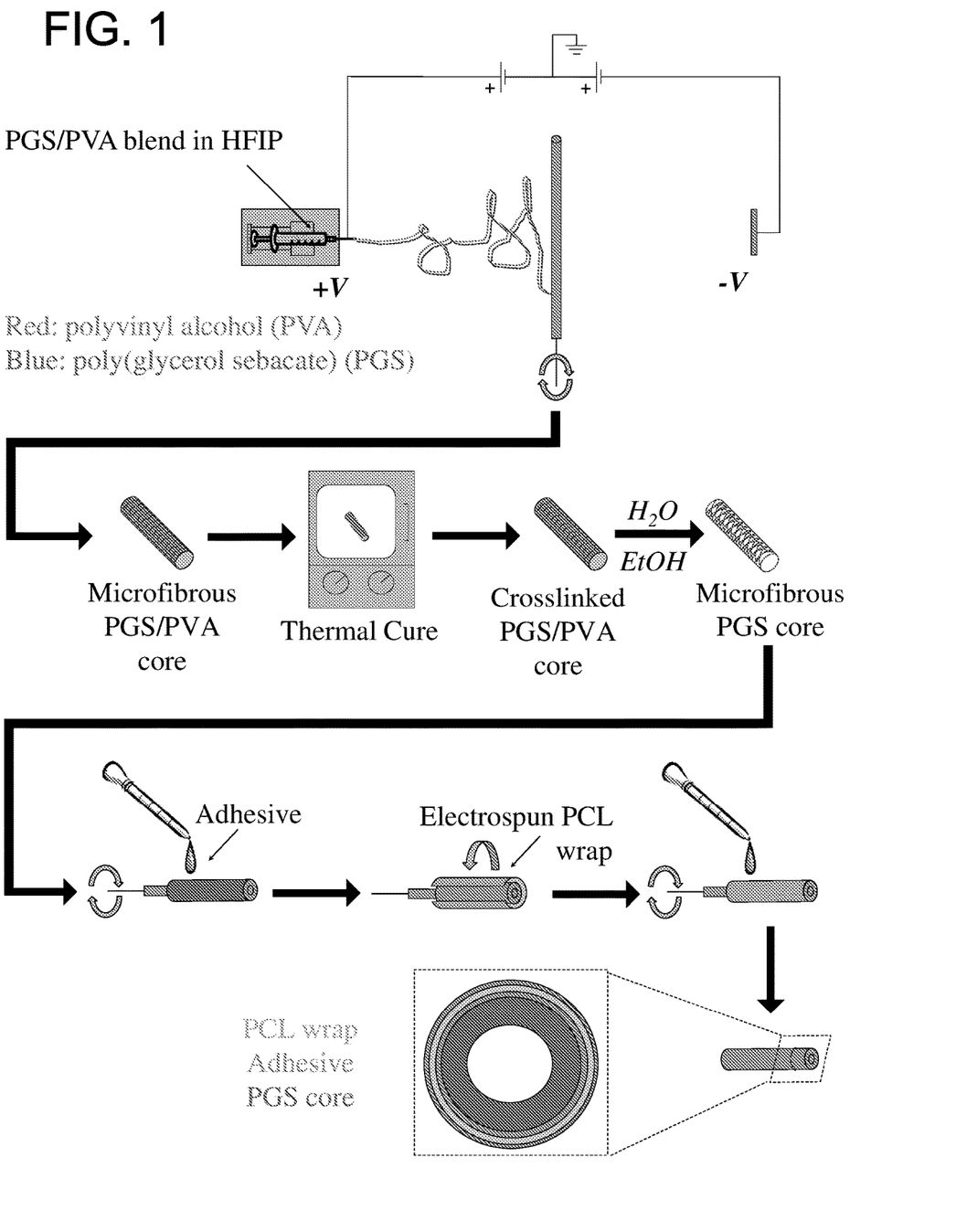
FIG. 1 is a schematic that shows one example of fabricating a scaffold as disclosed herein.

A method of fabricating a scaffold in shown in FIG. 1. A tubular PGS core was electrospun, cured, and washed as described in Jeffries et al. (*Acta Biomater.* 18: 30-39, 2015) which is hereby incorporated by reference in its entirety.

Poly(ε-caprolactone) was dissolved at 0.14 g per 0.8 ml trifluoroethanol and 0.2 ml distilled water. The solution was electrospun from a needle charged to 10 kVDC onto a conducting collector at −10 kVDC positioned 17 cm from the needle tip. An aluminum mandrel was rotated 2 cm from the collector, such that fibers landing on the collector were drawn to the mandrel. A longitudinal cut down the mandrel allowed the electrospun tube to be splayed out as a sheet.

The washed PGS core was soaked in saturated sodium chloride solution and lyophilized, which stiffened the core and partially packed the pores between fibers with salt crystals. The core was placed on a rotating mandrel (450 rpm for a core with an outer diameter of approximately 6.3 mm). Coats of poly(L-lactide-co-ε-caprolactone) dissolved at 0.025 g per 1 ml dichloromethane were pipetted onto the core at 240 ul per $cm^2$ of core surface area. Subsequently, an equal amount of poly(L-lactide-co-ε-caprolactone) dissolved at 0.025 g per 1 ml acetone was applied in the same way. Each coat was dried for 2 min under airflow produced by the mandrel rotation, then 3 min with rotation and laboratory house air flow. This procedure created a uniform base coat of adhesive on the core.

A coat of poly(L-lactide-co-ε-caprolactone) dissolved at 0.025 g per 0.1 ml dichloromethane and 0.9 ml acetone was pipetted onto the core at 50 ul per $cm^2$ of core surface area. Immediately the poly(ε-caprolactone) sheet was wrapped around the core. Fibers were fused at specific points along the seam by application of a hot needle. 240 ul per $cm^2$ additional solution of poly(L-lactide-co-ε-caprolactone) dissolved at 0.025 g per 1 ml acetone were applied per $cm^2$ of surface area as before. A brief wash in distilled water dissolved the salt from the core.

The electrospun core had a dry porosity of 71±3% and a residual polyvinyl alcohol content of 9.7±2.5%. Residual polyvinyl alcohol content was measured using differential scanning calorimetry; the area under the polyvinyl alcohol melting peak at approximately 18° C. was compared to a standard curve constructed using films with known poly (glycerol sebacate) and polyvinyl alcohol ratios. The core fiber diameter was 3.29±2.79 µm.

The composite graft was watertight to above 120 mmHg After pressurization to 120 mmHg and stretching to 10% axially for 66 h, the graft had <10% residual strain longitudinally and <20% circumferentially. Composite reinforcement increased the suture retention strength of the graft from 45±7 gf (electrospun core, thickness 600±77 µm) to 287±86 gf (core with adhesive-bonded electrospun poly(ε-caprolactone) sheet, combined thickness 129±33 µm). Suture retention testing used 6-0 Prolene with a 2 mm bite depth and a strain rate of 50 mm/min.

Reinforcement improved the circumferential incremental modulus from 127±37 to 2470±820 kPa and the ultimate tensile strength from 588±134 to 1510±640 kPa. The calculated burst pressure (assuming linear elastic deformation and taking the thin wall approximation) was in excess of 1000 mmHg Furthermore, grafts demonstrated more complete and rapid closure after needle puncture than did standard ePTFE grafts, which could allow cannulation of the graft soon after implantation and reduce workflow delays during implant and dialysis procedures. Composite grafts were implanted in pigs as carotid arteriovenous shunts. The animals were maintained on aspirin. At 15 d, H&E staining indicated cell infiltration and ECM deposition proceeding radially outwards from the lumen through approximately ⅔ of the wall. Possible endothelial, intimal, and medial layers were observed. Putative endothelial cells expressed CD31. Seven such grafts have been successfully implanted in ovine and porcine interposition and arteriovenous shunt models.

Comparative Results (1) A solid poly(ε-caprolactone) coat was attempted as the only external reinforcement. The coating was ductile, giving it poor suture retention, and the graft could not be implanted.

(2) A solid poly(L-lactide-co-ε-caprolactone) coat was attempted as the only external reinforcement. Under a sustained stretch of 10% and pressure of 120 mmHg in vitro, the graft dilated within three days and displayed axial stress relaxation, suggesting impending failure.

(3) Coats of poly(L-lactide-co-ε-caprolactone) in acetone only did not penetrate the PGS core sufficiently enough to produce sufficient adhesion.

In view of the many possible embodiments to which the principles of the disclosure may be applied, it should be recognized that the illustrated embodiments are only preferred examples of the invention and should not be taken as limiting the scope of the invention.

What is claimed is:

1. A vascular graft, comprising a biodegradable scaffold comprising:
   a biodegradable polyester electrospun tubular core;
   a biodegradable polyester outer sheath surrounding the biodegradable polyester tubular core; and
   a biodegradable poly(lactide) copolymer adhesive composition (i) disposed between the polyester electrospun tubular core and the polyester outer sheath, (ii) disposed between the polyester electrospun tubular core and the polyester outer sheath and on an outer surface of the polyester outer sheath, (iii) or disposed on an outer surface of the polyester outer sheath, wherein the poly(lactide) copolymer adhesive composition has a biodegradation rate that is between the biodegradation rate of the polyester electrospun tubular core and the biodegradation rate of the polyester outer sheath.

2. The graft of claim 1, wherein the poly(lactide) copolymer is selected from poly(lactide-co-caprolactone), poly(D,L-lactide-co-caprolactone), poly(D,L-lactide-co-glycolide), poly(L-lactide-co-glycolide), poly(L-lactide-co-caprolactone-co-glycolide), or a mixture thereof.

3. The graft of claim 1, wherein the poly(lactide) copolymer adhesive composition comprises poly(L-lactide-co-ε-caprolactone).

4. The graft of claim 1, wherein the poly(lactide) copolymer adhesive composition penetrates into at least a portion of the polyester outer sheath.

5. The graft of claim 1, wherein the biodegradable polyester electrospun tubular core comprises poly(glycerol sebacate) (PGS).

6. The graft of claim 1, wherein the biodegradable polyester sheath comprises poly(caprolactone) (PCL).

7. The graft of claim 1, further comprising a thromboresistant agent coating an inner lumen surface of the biodegradable polyester tubular core.

8. The graft of claim 7, wherein the thromboresistant agent comprises heparin.

9. The graft of claim 1, wherein the biodegradable polyester tubular core comprises small pores of about 10 μm to about 30 μm.

10. The graft of claim 1, wherein at least 95% of the vascular graft degrades within 90 days of implantation.

11. The graft of claim 1, wherein the vascular graft is cell-free.

12. A coronary or a peripheral arterial graft comprising the vascular graft of claim 1.

13. The graft of claim 1, wherein the poly(lactide) copolymer adhesive composition is disposed only between the polyester electrospun tubular core and the polyester outer sheath.

14. The graft of claim 1, wherein the poly(lactide) copolymer adhesive is disposed between the polyester electrospun tubular core and the polyester outer sheath and is disposed on an outer surface of the polyester outer sheath.

15. The graft of claim 1, wherein the poly(lactide) copolymer adhesive is disposed only on an outer surface of the polyester outer sheath.

16. The graft of claim 1, wherein the polyester outer sheath is a polyester electrospun outer sheath.

17. A vascular graft, comprising a biodegradable scaffold comprising:
   a biodegradable polyester electrospun tubular core;
   a biodegradable polyester outer sheath surrounding the biodegradable polyester tubular core; and
   a biodegradable poly(lactide) copolymer adhesive composition disposed only on an outer surface of the polyester outer sheath.

18. The graft of claim 17, wherein the poly(lactide) copolymer is selected from poly(lactide-co-caprolactone), poly(D,L-lactide-co-caprolactone), poly(D,L-lactide-co-glycolide), poly(L-lactide-co-glycolide), poly(L-lactide-co-caprolactone-co-glycolide), or a mixture thereof.

19. The graft of claim 17, wherein the poly(lactide) copolymer adhesive composition comprises poly(L-lactide-co-ε-caprolactone).

20. The graft of claim 17, wherein the poly(lactide) copolymer adhesive composition penetrates into at least a portion of the polyester outer sheath.

21. The graft of claim 17, wherein the biodegradable polyester electrospun tubular core comprises poly(glycerol sebacate) (PGS).

22. The graft of claim 17, wherein the biodegradable polyester sheath comprises poly(caprolactone) (PCL).

23. The graft of claim 17, further comprising a thromboresistant agent coating an inner lumen surface of the biodegradable polyester tubular core.

24. The graft of claim 17, wherein the biodegradable polyester tubular core comprises small pores of about 10 μm to about 30 μm.

25. The graft of claim 17, wherein at least 95% of the vascular graft degrades within 90 days of implantation.

26. The graft of claim 17, wherein the vascular graft is cell-free.

27. The graft of claim 4, wherein the poly(lactide) copolymer adhesive composition comprises poly(L-lactide-co-ε-caprolactone), the biodegradable polyester electrospun tubular core comprises poly(glycerol sebacate) (PGS), and the biodegradable polyester sheath comprises poly(caprolactone) (PCL).

28. The graft of claim 27, wherein the biodegradable polyester electrospun tubular core has small pores of 1 μm to 500 μm, and the biodegradable polyester sheath has a thickness between 5 μm and 30 μm.

29. The graft of claim 1, wherein the poly(lactide) copolymer adhesive composition has an elastic modulus of about 100 kPa to about 10 MPa.

30. The graft of claim 1, wherein the poly(lactide) copolymer adhesive composition has a strain recovery of at least 80% at 10% strain.

* * * * *